US00PP18440P2

(12) United States Plant Patent
Kops

(10) Patent No.: US PP18,440 P2
(45) Date of Patent: Jan. 15, 2008

(54) ***DAHLIA* PLANT NAMED 'KARMA ROYAL SEA'**

(50) Latin Name: *Dahlia hybrida*
Varietal Denomination: Karma Royal Sea

(75) Inventor: Nik Kops, Hillegom (NL)

(73) Assignee: Verwer Dahlias BV, Lisse (NL)

( * ) Notice: Subject to any disclaimer, the term of this patent is extended or adjusted under 35 U.S.C. 154(b) by 0 days.

(21) Appl. No.: 11/524,391

(22) Filed: Sep. 20, 2006

(51) Int. Cl.
*A01H 5/00* (2006.01)

(52) U.S. Cl. ..... Plt./321
(58) Field of Classification Search ..... Plt./321
See application file for complete search history.

(56) References Cited

PUBLICATIONS

GTITM UPOVROM Citation for 'Karma Royal Sea' as per QZ PBR 20052593; Dec. 8, 2005.*

* cited by examiner

*Primary Examiner*—Kent Bell
(74) *Attorney, Agent, or Firm*—C. A. Whealy

(57) ABSTRACT

A new and distinct cultivar of *Dahlia* plant named 'Karma Royal Sea', characterized by its upright and somewhat outwardly spreading plant habit; strong and erect peduncles; freely flowering habit; decorative-type inflorescence form; large inflorescences with deep red-colored ray florets; and good garden performance and postproduction longevity.

2 Drawing Sheets

Botanical designation: *Dahlia hybrida.*
Cultivar denomination: 'Karma Royal Sea'.

BACKGROUND OF THE INVENTION

The present invention relates to a new and distinct cultivar of *Dahlia* plant, botanically known as *Dahlia hybrida,* and hereinafter referred to by the name 'Karma Royal Sea'.

The new *Dahlia* is a product of a planned breeding program conducted by the Inventor in Hillegom, The Netherlands. The objective of the breeding program is to create new cut flower *Dahlia* cultivars that have a freely flowering habit, decorative inflorescence form, attractive ray floret coloration, and good postproduction longevity.

The new *Dahlia* originated from a cross-pollination in Hillegom, The Netherlands in 2002 of two unidentified selections of *Dahlia hybrida,* not patented. The new *Dahlia* was discovered and selected by the Inventor as a single flowering plant within the progeny of the stated cross-pollination in a controlled environment in Hillegom, The Netherlands in 2003.

Asexual reproduction of the new *Dahlia* by cuttings in a controlled environment in Lisse, The Netherlands, has shown that the unique features of this new *Dahlia* are stable and reproduced true to type in successive generations.

SUMMARY OF THE INVENTION

The cultivar Karma Royal Sea has not been observed under all possible environmental conditions. The phenotype may vary somewhat with variations in environment such as temperature and light intensity, without, however, any variance in genotype.

The following traits have been repeatedly observed and are determined to be the unique characteristics of 'Karma Royal Sea'. These characteristics in combination distinguish 'Karma Royal Sea' as a new and distinct cultivar of *Dahlia:*

1. Upright and somewhat outwardly spreading plant habit.
2. Strong and erect peduncles.

3. Freely flowering habit.
4. Decorative-type inflorescence form.
5. Large inflorescences with deep red-colored ray florets.
6. Good garden performance and postproduction longevity.

Compared to plants of the parent selections, plants of the new *Dahlia* differ primarily in plant size and ray floret color.

Plants of the new *Dahlia* can be compared to plants of the *Dahlia* cultivar Karma Naomi, disclosed in U.S. Plant Pat. No. 11,413. In side-by-side comparisons conducted in Lisse, The Netherlands, plants of the new *Dahlia* differed from plants of the cultivar Karma Naomi in the following characteristics:

1. Plants of the new *Dahlia* were shorter than plants of the cultivar Karma Naomi.
2. Plants of the new *Dahlia* were more freely branching than plants of the cultivar Karma Naomi.
3. Plants of the new *Dahlia* were more freely flowering than plants of the cultivar Karma Naomi.
4. Inflorescences of plants of the new *Dahlia* had longer postproduction longevity than plants of the cultivar Karma Naomi.

BRIEF DESCRIPTION OF THE PHOTOGRAPHS

The accompanying photographs illustrate the overall appearance of the new *Dahlia.* The photographs shows the colors as true as it is reasonably possible to obtain in colored reproductions of this type. Colors in the photographs may differ slightly from the color values cited in the detailed botanical description which accurately describe the colors of the new *Dahlia.*

The photograph on the first sheet comprises a side perspective view of typical flowering plants of 'Karma Royal Sea' grown in an outdoor nursery.

The photograph on the second sheet is a close-up view of a typical inflorescence of 'Karma Royal Sea'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lisse, The Netherlands during the summer in an outdoor nursery and under conditions and practices which approximate those generally used in commercial *Dahlia* production. During the production of the plants, day temperatures ranged from 15° C. to 30° C. and night temperatures ranged from 10° C. to 20° C. Plants were pinched one time about three to four weeks after planting. Measurements and numerical values represent averages for typical flowering plants. Plants were about four months old when the photographs and description were taken.

Botanical classification: *Dahlia hybrida* cultivar Karma Royal Sea.

Parentage:

*Female, or seed, parent.*—Unidentified selection of *Dahlia hybrida,* not patented.

*Male, or pollen, parent.*—Unidentified selection of *Dahlia hybrida,* not patented.

Propagation:

*Type.*—By cuttings.

*Time to initiate roots, summer.*—About ten days at temperatures of about 18° C.

*Time to initiate roots, winter.*—About twelve days at temperatures of about 18° C.

*Time to produce a rooted young plant, summer.*—About 24 days at temperatures of about 18° C.

*Time to produce a rooted young plant, winter.*—About 27 days at temperatures of about 18° C. to 20° C.

*Root description.*—Fine to fleshy; tuber development has not been observed.

*Rooting habit.*—Freely branching; dense.

Plant description:

*Plant form/growth habit.*—Upright to somewhat outwardly spreading; inverted triangle plant form. Freely basal branching with about four to six lateral branches and inflorescences held above the foliage on strong peduncles; bushy and dense. Moderately vigorous growth habit.

*Plant height.*—About 110 cm.

*Plant diameter or spread.*—About 45 cm.

*Lateral branches.*—Length: About 20 cm to 25 cm. Diameter: Towards the base, about 5 mm; towards the apex, about 2 mm. Internode length: About 5 cm to 22 cm. Aspect: Erect to somewhat outwardly spreading. Strength: Strong. Texture: Smooth, glabrous. Color: 146C tinted with 178A.

Foliage description:

*Arrangement.*—Leaves opposite; leaves may be single or compound with three or five leaflets.

*Shape.*—Ovate.

*Apex.*—Aristulate.

*Base.*—Attenuate.

*Margin.*—Serrate and divided; sinuses divergent.

*Length.*—Single leaves: About 8 cm. Compound leaves with three leaflets: About 13 cm. Compound leaves with five leaflets: About 16 cm.

*Width.*—Single leaves: About 3 cm. Compound leaves with three leaflets: About 9 cm. Compound leaves with five leaflets: About 15 cm.

*Venation pattern.*—Pinnate.

*Texture, upper and lower surfaces.*—Smooth, glabrous.

*Color.*—Developing foliage, upper surface: 144A. Developing foliage, lower surface: 147C. Fully expanded foliage, upper surface: Darker than 141A; venation, 151C. Fully expanded foliage, lower surface: 147C; venation, 151A.

*Petiole length.*—Single leaves: About 0.5 cm. Compound leaves with three leaflets: About 3 cm. Compound leaves with five leaflets: About 3 cm.

*Petiole diameter.*—Single leaves: About 3 mm. Compound leaves with three leaflets: About 3 mm. Compound leaves with five leaflets: About 3 mm.

*Petiole texture, upper and lower surfaces.*—Smooth, glabrous.

*Petiole color, upper and lower surfaces.*—152A.

Inflorescence description:

*Appearance.*—Rotate single inflorescence form with ray and disc florets. Inflorescences positioned above the foliage on strong peduncles. Inflorescences face upright to slightly outwardly. Freely flowering habit; about 30 inflorescences develop per plant. Inflorescences persistent. Inflorescences not fragrant.

*Time to flower.*—Plants flower continuously during the summer and autumn in The Netherlands.

*Post-production longevity.*—Good postproduction longevity; inflorescences maintain good substance for about 30 days on the plant and for about eleven days as a cut flower.

*Inflorescence bud.*—Height: About 1.3 cm. Diameter: About 2.1 cm. Shape: Oblate. Color: 151A.

*Inflorescence size.*—Diameter: About 12 cm. Depth (height): About 9 cm. Disc diameter: About 2 cm. Receptacle height: About 3 cm. Receptacle diameter: About 3 cm.

*Ray florets.*—Length: About 5.5 cm. Width: About 1.6 cm. Shape: Ovate to elliptical. Apex: Acuminate. Base: Attenuate. Aspect: Initially upright to roughly perpendicular to the peduncle to reflexed; flat or slightly cupped. Texture, upper and lower surfaces: Smooth, glabrous; satiny. Number of ray florets per inflorescence: About 128 arranged in about 16 whorls. Color: When opening, upper surface: 183A. When opening, lower surface: 183C; towards the center, 75B. Fully opened, upper surface: 53A; toward the base, 31A. Fully opened, lower surface: 53B; towards the center, 75B.

*Disc florets.*—Shape: Tubular; apex dentate. Length: About 3 mm. Diameter, apex: About 0.2 mm. Diameter, base: About 0.2 mm. Number of disc florets per inflorescence: About 60. Color: Immature: 1D. Mature: Apex and mid-section: 17A. Base: 1D.

*Phyllaries.*—Quantity per inflorescence: About eight arranged in a single whorl. Length: About 1.5 cm. Width: About 4 mm. Shape: Ovate to lanceolate. Apex: Acuminate. Base: Attenuate. Margin: Entire. Texture, upper and lower surfaces: Smooth, glabrous; satiny. Color, upper surface: 144A with longitudinal stripes, 175B. Color, lower surface: 144A.

*Peduncles.*—Length: Terminal peduncle: About 25 cm. Fourth peduncle: About 10 cm. Seventh peduncle: About 8 cm. Diameter: About 9 mm. Strength: Strong. Aspect: Erect to about 10° from vertical. Texture: Smooth, glabrous. Color: 187B.

*Reproductive organs.*—Androecium: Quantity per disc floret: Five. Anther shape: Linear. Anther length: About 0.1 mm. Anther color: 17B. Pollen amount:

Scarce. Pollen color: 21B. Gynoecium: Quantity per ray or disc floret: One. Pistil length: About 2 mm. Stigma shape: Lanceolate. Stigma color: 2C. Style length: About 1 mm. Style color: 1D. Ovary color: 178B. Seeds: Seed development has not been observed.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Karma Royal Sea' as illustrated and described.

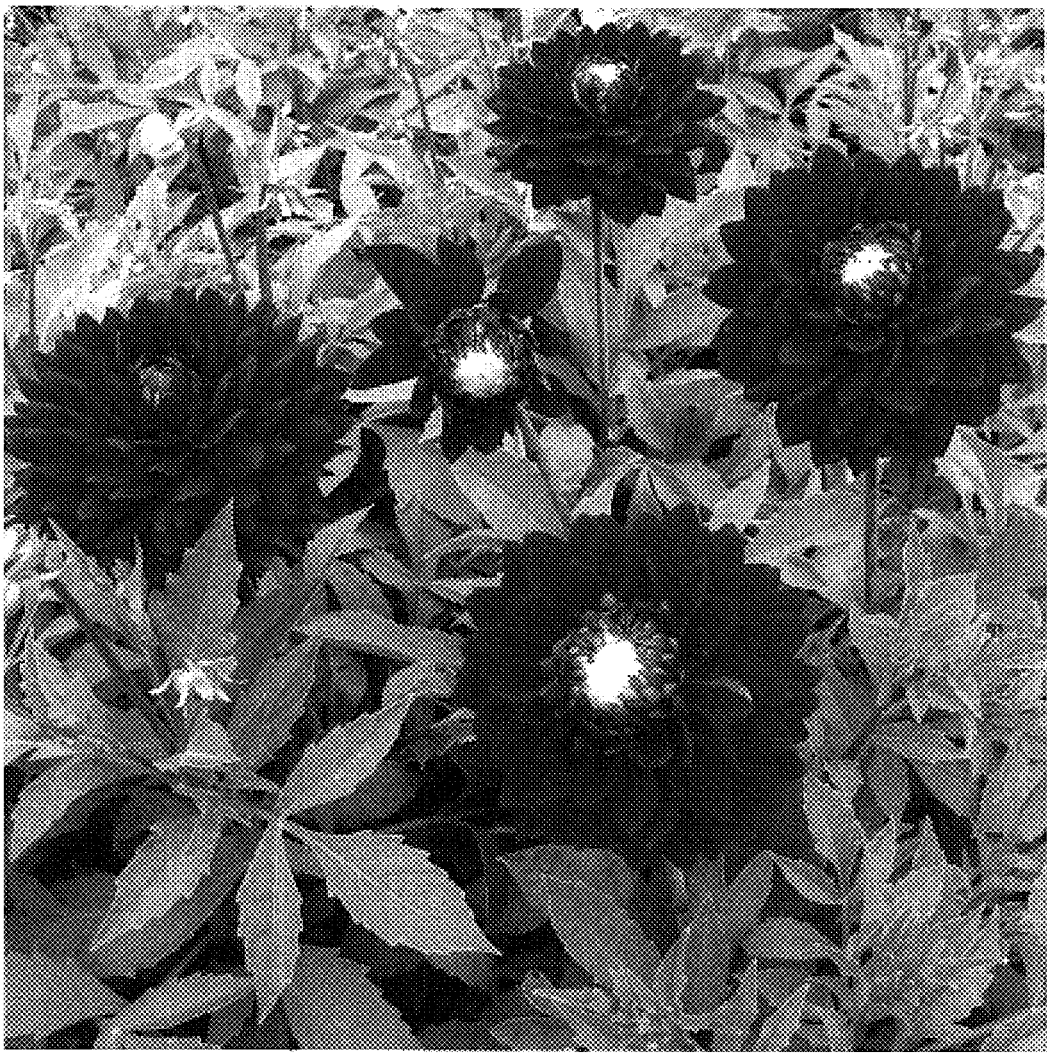

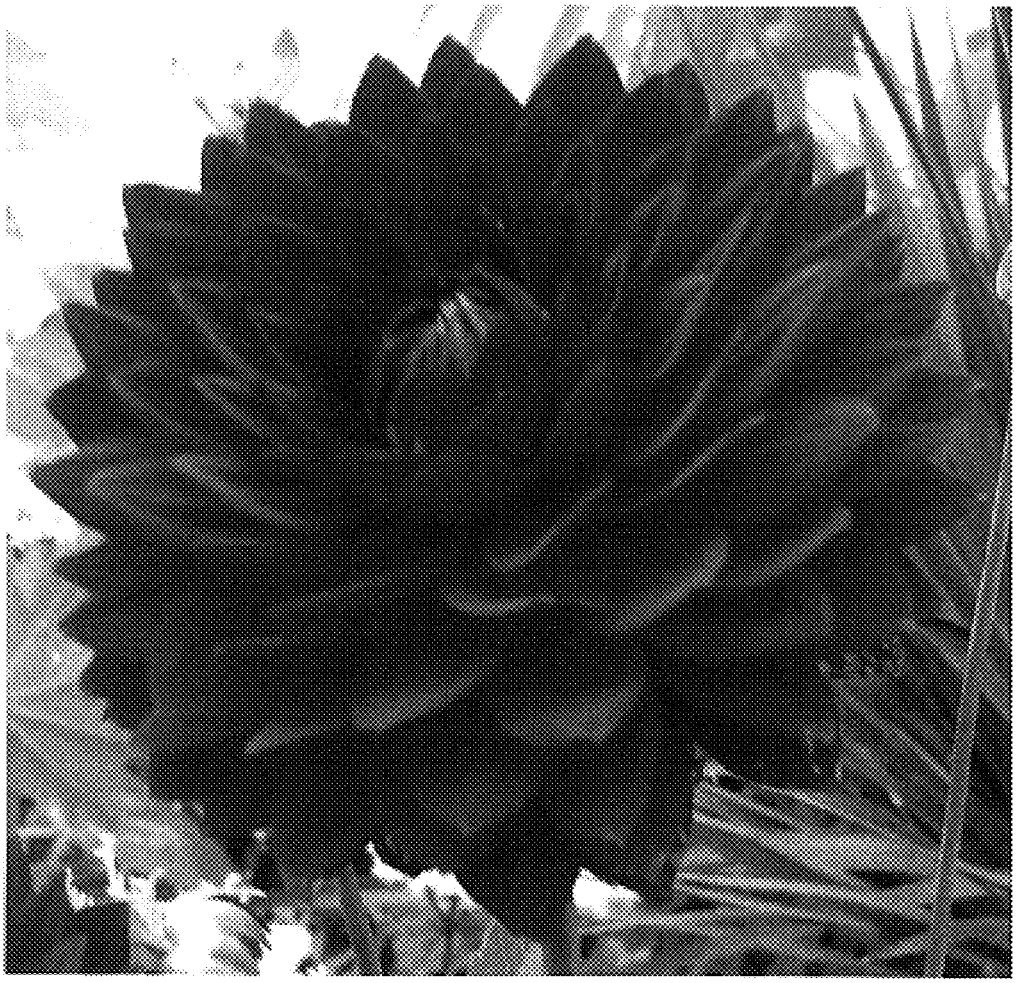

* * * * *